United States Patent [19]

Wysor

[11] 4,415,565

[45] Nov. 15, 1983

[54] SILVER METACHLORIDINE IN TREATMENT OF INFECTIONS

[75] Inventor: Michael S. Wysor, Washington, D.C.

[73] Assignee: The United States of America as represented by the Secretary of the Army, Washington, D.C.

[21] Appl. No.: 246,984

[22] Filed: Mar. 24, 1981

Related U.S. Application Data

[62] Division of Ser. No. 135,059, Mar. 18, 1980, Pat. No. 4,384,117.

[51] Int. Cl.³ .......................................... A61K 31/555
[52] U.S. Cl. .................................................. 424/245
[58] Field of Search ........................................ 424/245

Primary Examiner—Jerome D. Goldberg
Attorney, Agent, or Firm—William G. Gapcynski; Werten F. W. Bellamy

[57] ABSTRACT

The silver salt of metachloridine has been shown to have marked effectiveness against viruses, bacteria, fungi and protozoa. It is active against the organisms over a considerable concentration range in vitro, and has a noteworthy, high chemotherapeutic index when administered to animals by topical, oral or parenteral route. In addition to its effectiveness, silver metachloridine has been shown to be well tolerated at levels far above those required for therapeutic uses in animals.

8 Claims, No Drawings

SILVER METACHLORIDINE IN TREATMENT OF INFECTIONS

GOVERNMENT RIGHTS

The invention described herein may be manufactured and used by or for the Government, for governmental purposes, without the payment of any royalties thereon.

This is a division, of application Ser. No. 135,059, filed Mar. 18, 1980, now U.S. Pat. No. 4,384,117 issued May 17, 1983.

BACKGROUND OF THE INVENTION

This invention relates generally to silver metachloridine compositions, and more particularly to the oral, systemic, or topical administration of that silver salt for the treatment or control of infections.

The existence of silver salts of p-aminobenzene sulfonamides and their chemotherapeutic activity are known. Relevant to chemotherapeutic effectiveness of such silver salts of sulfanilamide and congeners are U.S. Pat. Nos. 2,422,688; 3,761,590; and 4,020,150.

Compositions containing silver sulfadiazine have been shown to have broad microbiocidal effectiveness while being well tolerated by man and animals. Such compositions do also exhibit few untoward actions on the host while exerting desirable therapeutic effects. The stability of such compositions under a variety of conditions has been of marked consequence in their practical use. Applicant has determined that the silver salt of sulfadiazine is of unexpectedly complex character and appears to exist in two different forms, possibly of differing polymeric structures. Such structural features of that silver salt of a sulfanilamide derivative may well provide substantive basis for its profile of activity and lack of appreciable toxic effects, inclusive of argyrism.

The instant invention relates to the novel development of a microbiocidally effective silver salt of metachloridine which may be administered topically, orally, or systemically for treatment or control of various infections caused by diverse organisms, such as viruses, bacteria, fungi, or protozoa. It teaches a practical means for preparing the novel silver salt of metachloridine and methods for its use as a microbiocidal agent through evaluation under standardized laboratory tests which demonstrate its superiority over the silver salt of sulfadiazine.

The structures of sulfadiazine (I) and metachloridine (II) are hereinafter depicted. It is readily seen that (I) is chemically describable as 2-sulfanilaminidopyrimidine, and (II) is 5-chloro-2-metanilamidopyrimidine. Thus, although both compounds are relatable to a parent 2-aminopyrimidine, there are several clear differences in structure. Compound (I) is an N-2-pyrimidinyl derivative of sulfanilamide, which is 4-aminobenzenesulfonamide. Compound (II) is a derivative of metanilamide (3-aminobenzenesulfonamide) which further differs from (I) in the presence of a chlorine substituent (Cl grouping) at position 5 of the heterocyclic pyrimidine moiety. Each of the drugs (I) and (II) have been assessed in detail from the standpoint of microbiocidal effects and toxicological-pharmacological profiles in man as well as lower animals.

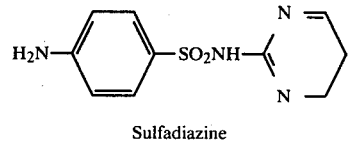

Sulfadiazine

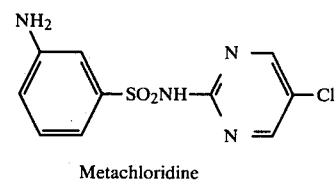

Metachloridine

Practical utility of the silver salt of sulfadiazine has been demonstrated. In particular, the micronized drug has been incorporated into a water-miscible cream as an adjunct for the management of wounds, especially in prevention and treatment of sepsis in severe burns. A mode of action distinct from the silver salts and also sulfadiazine has been indicated for silver sulfadiazine, which has shown a low incidence of untoward effects in thousands of unselected cases. From laboratory studies, polymeric character has been indicated for both the silver salt of sulfadiazine and the herein described silver salt of metachloridine. In biological testing, the superiority of the novel product, silver metachloridine has been demonstrated over the previously known silver sulfadiazine. Allied 2-metanilamidopyrimidines, such as described by J. P. English, et. al. (J. Am. Chem. Soc., 68, 1039–1049 (1946), are also anticipated being useful in manufacture of congener silver salts having similar profiles of microbiocidal effectiveness and chemotherapeutic worth evident in the silver salt of metachloridine.

Regarding metachloridine, note must be taken that that particular sulfonamide itself, was the subject of considerable investigation during World War II. Under the designation SN-11 437, metachloridine was studied extensively as a candidate antimalarial agent: F. Y. Wiselogle, editor, "A Survey of Antimalarial Drugs, 1941–1945" (Edwards Brothers, Ann Arbor, Michigan, 1946), volumes I and II. SN-11 437 was sufficiently active in screening tests for antimalarial effects that it was given detailed chemotherapeutic and pharmacological evaluation. (loc. cit., volume I, pp. 294–299).

SUMMARY OF THE INVENTION

This invention relates to novel means for affording treatment or control of infections in mammalian species which may be caused by viruses, bacteria, fungi, or protozoa. It is based upon the use or administration of therapeutically effective amounts of the silver salt of metachloridine by topical, oral, or parenteral route. In the presence of trichomonal vaginitis, and/or vaginal thrush infections, subject drug may be applied intravaginally in appropriate vehicle. Under conditions of therapeutic use, subject silver salt of metachloridine is well tolerated by animals and has advantages over silver sulfadiazine in better chemotherapeutic index. The improvements in efficacy and safety over silver sulfadiazine achievable with silver metachloridine will be apparent from the detailed description of the specific embodiments of this invention.

DETAILED DESCRIPTION OF THE INVENTION

Practical utility has been established for silver sulfadiazine as a microbiocidal agent. Silver metachloridine is a species of silver salt of a different sulfonamide type, such as is evident in comparison of structures (I) and (II). The development of silver metachloridine as a microbiocidal agent for topical, oral or parenteral use will be shown hereinafter to constitute a clear advance over silver sulfadiazine as demonstrated by standard means for laboratory evaluation, and by selective intercomparison of the two drugs.

Compositions of subject silver metachloridine embody those which may be preferable for the specific mode for its use. Vehicles for achieving uniform topical application may include: solutions (as, in a menstruum containing dimethyl sulfoxide); or creams (as, a vanishing cream base); or, ointment (as, white or yellow ointment); or, liniment (as, green soap tincture); or, a malagma (as, an emollient oil). Such vehicles could be selected appropriately, depending upon circumstances of need for modulating the microbiocidal effects of silver metachloridine. Thus, advantages may be gained by micronizing the drug when not used in solution form. Toward appropriate form for intravaginal use of silver metachloridine, the drug may be advantageously incorporated into suppositories having water soluble base, or jellies, or creams, or foams also having hydrosoluble base. For oral administration, the drug may be formulated in tablets or capsules or dragées as when admixed with solid excipients such as lactose, sucrose, microcrystalline cellulose, as alkal, metal bicarbonate such as sodium bicarbonate starch, talc, or magnesium stearate. Under such circumstances, micronized silver metachloridine may demonstrate especial efficacy. The foregoing may be preferred over oral use of the drug in flavored suspensions, syrups, or tinctures. Silver metachloridine may also be incorporated in various oleaginous vehicles (as, benzyl benzoate or peanut oil) for depot formulations as well as in other media commonly used for giving drugs.

MATERIALS AND METHODS

Instant invention discloses the preparation of the silver salt of metachloridine and demonstration of its efficacy in use under laboratory conditions. This has been toward the aim and goal of establishing utility under reproducible, closely controlled conditions. Such firm bases for testing and evaluation have been requisite both for showing worth of silver metachloridine and for intercomparison with silver sulfadiazine, thereby affording evidence of the superiority of silver metachloridine.

MATERIALS

Metachloridine (5-chloro-2-metanilamidopyrimidine) was a crystalline product (m.p. 22 229°, dec.) made after the published method of J. P. English, et. al. (loc. cit.). The substances used in conversion of metachloridine into its silver salt (as hereinafter described) were of laboratory reagent quality to ensure uniformity.

Silver metachloridine

One mole of metachloridine is reacted with one mole of silver nitrate to yield one mole of silver metachloridine. The reaction is carried out in an ammonium hydroxide medium. Using the 1:1 stoichiometry, the synthesis of 100 grams of silver metachloridine would be carried out in the following manner: 100 grams metachloridine (0.351 moles) is suspended in 500 ml of water, then concentrated ammonium hydroxide is added gradually to the stirred metachloridine-water mixture until the solid metachloridine goes into solution. 60 grams of silver nitrate is then added to 250 ml water to which solution there is then added 40 ml of ammonium hydroxide. More ammonia water is then added until the brown precipitate becomes a clear silver-ammine solution. A stirring bar is then placed into the silver-ammine solution and the solution is stirred. The metachloridine-ammine solution is then filtered several times, including once through activated charcoal. On the last filtering, place the metachloridine-ammine filter so that the metachloridine drops into the stirring silver-ammine solution. Product forms immediately, and is collected and dried. The chemical structure for silver metachloridine is unknown at the present time.

METHODS

1. Antibacterial Screening

Screening by the method of Carr et. al.:
Carr, D.; Wlodkowski, T. J.; and Rosenkranz, H. S.: In Vitro Antibacterial Activity, *Antimicrob. Ag. & Chemotherp.*, 5:585–587, 1973.

2. Antifungal Screening

Screening by the following methods:
Wlodkowski, T. J.; and Rosenkranz, H. S.: Antifungal Activity of Silver Sulfadiazine. Lancet, ii, 739–740, 1973.
Speck, W. T.; and Rosenkranz, H. S.: Activity of Silver Sulfadiazine Against Surface Dermatophytes. Lancet, ii, 895–896, 1974.

3. Antiviral Screening

Screening by the following methods:
Chang, T. W.; and Weinstein, L.: In Vitro Activity of Silver Sulfadiazine Against Herpes Virus Hominis. *J. Inf. Dis.*, 132:79–81, 1975.
Tokumaru, T.; Shimizu, Y.; and Fox, C. L., Jr.: Antiviral Activities of Silver Sulfadiazine in Ocular Infection. *Res. Commun. Chem. Pathol. Pharmacol.* 8:151–158, 1974.
Steven, E.: Report Anti-viral Chemotherapy Section, USAMIIRD, U.S. Army Medical Research and Development Command, Ft. Detrick, Md.

4. Antiprotozoan Screening

A. Screening by the following in vitro methods:

Malaria: (*P. falciparum*)

Desjardins, R. E.; Canfield, C. J.; Haynes, J. D.; and Chulay, J. D.: Quantitative Assessment of Antimalarial Activity In Vitro by A Semi-automated Microdilution Technique. *Antimicrob. Ag. & Chemother.*, 16:710–718, 1979.

Trypanosomes (*T. rhodesiense*)

Desjardins, R. E.; Casero, R. A., Jr.; Willet, G. P.; Childs, G. E.; and Canfield, C. J.: *Trypanosoma rhodesiense*: A Semi-automated Microtest System for Quantitative Assessment of Antitrypanosomal Activity In Vitro. *Exptl. Parasitol.* (in press)

Trypanosomes (*T. cruzi*)

10 mg/ml of drug was suspended in distilled water and allowed to settle. The supernatant was then removed and then diluted to testing *T. cruzi* was grown according to the following method:

Evans, D. A.; *Kinetoplastida* in *Methods of Cultivating Parasites In Vitro*. Angela E. R. Taylor and John Baker (eds.), Academic Press, 1976.

Trichomonads (*T. vaginalis*)

Bruckner, D. A. and Bueding, E.: Lack of Obligatory Association Between Mutagenic and Antitrichomonal Effects of Metronidazole. *J. Parasitol.* 65:473–474, 1979.

Leishmania (*L. braziliensis*)

Hendricks, L. D.: An In Vitro Drug Screening System for Leishmania Using Axenically Derived Amastigotes. Published as a short communication in Abstracts of the 4th International Congress Parasitology, 19–26 August 1978, Warsaw, Poland, Section D-6, p. 87.

B. *T. rhodesiense* screening in mice performed after the method of L. Rane, D. S. Rane, and K. E. Kinnamon: *Am. J. Trop. Med. Hyg.*, 25:395–400, 1978. The screen was modified by the administration of the drugs in water four times per day for seven days. Adequate hydration was maintained by the subcutaneous injection of physiological saline (2.5 ml) four times per day for seven days.

5. Toxicity

Wysor, M. S.: Orally-Administered Silver Sulfadiazine; Chemotherapy and Toxicology in CF-1 Mice, *Plasmodium berghei* (Malaria) and *Pseudomonas Aeruginosa*. Chemotherapy, 21:298–306, 1975.

The following examples are illustrative, without implied limitation of my invention.

EXAMPLE 1

Silver Metachloridine: Antibacterial Screening

Silver metachloridine, like silver sulfadiazine has a broad spectrum of activity against gram positive and gram negative organisms, including Pseudomonas species. The broad spectrum activity of silver sulfadiazine against bacteria is well documented. (See Physicians' Desk Reference under "Silvadene®", 33rd Ed., 1979, p. 1085, Wlodkowski and Rosenkranz, Lancet, 2:739, 1973.)

EXAMPLE 2

Silver Metachloridine: Antifungal Screening

Silver metachloridine, like silver sulfadiazine has a broad spectrum of activity against fungal species such as *Candida albicans* and surface dermatophytes. The broad spectrum anti-fungal activity of silver sulfadiazine is well documented. (See Physicians' Desk Reference under "Silvadene®", 33rd Ed., 1979, p. 1085, Wlodkowski and Rosenkranz, Lancet, 2:738–740, 1974, Speck and Rosenkranz, Lancet, 3:895–896, 1974).

EXAMPLE 3

Silver Metachloridine: Antiviral Screening

Viruses: Silver metachloridine and silver sulfadiazine were tested and compared with Ribavirin, a new, experimental anti-viral agent. Results were as follows:

EFFECT OF VARIOUS ANTIVIRAL COMPOUNDS ON VIRUS YIELD AS MEASURED BY PLAQUE ASSAY

| Virus (cell type) | Concentration required to give 80% plaque reduction ($\mu$g/ml) | | |
|---|---|---|---|
| | Ribavirin | AgSD[a] | AgMeta in DMSO[a] |
| RVFV (SW-13) | 25 | 5 | 2.5 |
| YF (MK-2) | 50 | — | greater than 10[b] |
| VEE (VERO) | 100 | 10 | 10 |
| DEN-2 (SW-13) | 100 | greater than 2.5 | greater than 2.5 |
| SFS (SW-13) | 100 | greater than 2.5 | — |
| PICH (VERO) | 100 | greater than 10 | — |

[a] Toxic to tissue culture at 5 $\mu$g/ml and up
[b] DMSO control had similar plaque reduction The toxicity of the drugs to the tissue culture is an artifact caused by the particulate nature of the drug. In vivo experiments suggest that these silver compounds are not toxic to cells.

EXAMPLE 4

Silver Metachloridine: Antiprotozoal Screening

In addition to the in vitro results for trypanosomes and falciparum malaria, silver metachloridine had activity against the following organisms:

1. Leishmania braziliensis

Silver metachloridine completely inhibited growth and transformation of axenic amastigotes in vitro at the maximum solubility of the drug for 96 hours exposure. The drug was better than the antimonials Glucantime ® and Pentostam ® which were used as controls.

| *Plasmodium falciparum*: | $ED_{50}$ (nanograms/ml) |
|---|---|
| silver metachloridine | 0.7 |
| silver sulfadiazine | 114.0 |
| metachloridine | out-of-range* |
| sulfadiazine | out-of-range* |

*greater than 12.50 $\mu$g/ml

IN VITRO RESULTS

| *Trypanosoma rhodesiense*: | $ED_{50}$ ($\mu$g/ml) | |
|---|---|---|
| compound | $^3$H-Thymidine | $^{14}$C-Leucine |
| silver metachloridine | 5.0 | 10.3 |
| silver sulfadiazine | 5.1 | out-of-range* |
| silver sulfameter | 4.6 | out-of-range |
| silver sulfadoxine | out-of-range | out-of-range |
| silver sulfalene | out-of-range | out-of-range |
| zinc sulfadiazine | out-of-range | out-of-range |
| aluminum sulfadiazine | out-of-range | out-of-range |
| metachloridine | out-of-range | out-of-range |
| sulfadiazine | out-of-range | out-of-range |
| sulfameter | out-of-range | out-of-range |
| sulfadoxine | out-of-range | out-of-range |
| sulfalene | out-of-range | out-of-range |

*greater than 12.50 $\mu$g/ml

IN VIVO RESULTS

Silver metachloridine is effective against *T. rhodesiense* in mice when administered at a dosage of 500 mg/kg/dose, four times per day for one week. Silver metachloridine when used at maximum solubility, and when such supernatant material (in water) is placed in a suitable carrier such as a liposome results in marked activity in hamsters against visceral leishmaniasis.

2. *Trypanosoma cruzi* (Chagas' Disease)

Silver metachloridine was tested against epimastigote forms of T. (S.) cruzi in vitro. The drug at maximum solubility completely inhibited the organism, with activity seen at six hours post exposure. Only ghost forms were detectable in the culture at that time. Activity was still evident at a 1:20 dilution of the supernatant.

3. *Trichomonas vaginalis*

Silver metachloridine is trichomonistatic against this organism in vitro at maximum solubility.

EXAMPLE 5

Silver Metachloridine: Toxicity

Silver metachloridine was well tolerated in oral doses of 1 gram per kilogram body weight in mice, by the oral route. The drug has been administered in doses of 1 gram/kilogram four times per day for one week without any acute toxicity. Silver metachloridine, like silver sulfadiazine, was toxic when administered by the i.p. route (in water), but well tolerated in peanut oil and other similar agents. To prevent crystalluria, adequate hydration was maintained.

I claim:

1. A method for treating topical or systemic infections caused by bacteria, fungi species, viruses, or protozoa comprising the step of administering topically, intravaginally, parenterally, or orally to an infected animal an effective bacteriacidal, fungicidal, antiviral or protozoacidal amount of silver metachloridine.

2. The method of claim 1 wherein silver metachloridine is administered by parenterally or orally.

3. The method of claim 1 wherein silver metachloridine is administered topically.

4. The method of claim 1 wherein silver metachloridine is administered intravaginally for treating infections of the female genital tract.

5. A method for treating topical or systemic infections caused by bacteria, fungi species, viruses, or protozoa comprising the step of administering orally to an infected animal an effective bacteriacidal, fungicidal, antiviral or protozoacidal amount of a mixture of silver metachloridine and a carrier substance selected from the group comprising lactose, microcrystalline cellulose, an alkali metal bicarbonate, starch, talc, or magnesium stearate.

6. The method of claim 5 wherein the alkali metal bicarbonate is sodium bicarbonate.

7. A method for treating topical or systemic infections caused by bacteria, fungi species, viruses, or protozoa comprising the step of administering intravaginally to an infected animal an effective bacteriacidal, fungicidal, antiviral or protozoacidal amount of a mixture comprising silver metachloridine and (a) a suppository containing a water soluble base, or (b) a jelly, cream or foam containing a water soluble base.

8. A method for treating topical or systemic infections caused by bacteria, fungi species, viruses, or protozoa comprising the step of administering topically to an infected animal an effective bacteriacidal, fungicidal, antiviral or protozoacidal amount of a mixture comprising silver metachloridine and a carrier substance comprising dimethyl sulfoxide, vanishing cream base, white or yellow oinment, liniment or a malagma.

* * * * *